US007985423B2

(12) United States Patent
Cooper et al.

(10) Patent No.: US 7,985,423 B2
(45) **Date of Patent: *Jul. 26, 2011**

(54) POROUS BODIES AND METHOD OF PRODUCTION THEREOF

(75) Inventors: Andrew Ian Cooper, Liverpool (GB); Alison Jayne Foster, Wirral (GB); Steven Paul Rannard, Wirral (GB); Haifei Zhang, Liverpool (GB)

(73) Assignee: IOTA NanoSolutions Limited, London (GB)

( * ) Notice: Subject to any disclaimer, the term of this patent is extended or adjusted under 35 U.S.C. 154(b) by 849 days.

This patent is subject to a terminal disclaimer.

(21) Appl. No.: 10/587,722

(22) PCT Filed: Dec. 23, 2004

(86) PCT No.: PCT/EP2004/014755

§ 371 (c)(1),
(2), (4) Date: Jul. 27, 2006

(87) PCT Pub. No.: WO2005/075546

PCT Pub. Date: Aug. 18, 2005

(65) Prior Publication Data

US 2008/0226721 A1 Sep. 18, 2008

(30) Foreign Application Priority Data

Jan. 28, 2004 (GB) .................................. 0401947.7

(51) Int. Cl.

| | |
|---|---|
| ***A61K 8/72*** | (2006.01) |
| ***C08J 9/28*** | (2006.01) |
| ***A61Q 19/00*** | (2006.01) |
| ***A61Q 5/00*** | (2006.01) |

(52) U.S. Cl. ........ 424/486; 521/146; 521/149; 521/150; 521/155; 521/154; 521/182; 521/189; 521/64; 424/401; 424/59; 424/62; 424/70.11

(58) Field of Classification Search .................. 424/486
See application file for complete search history.

(56) References Cited

U.S. PATENT DOCUMENTS

| | | | | |
|---|---|---|---|---|
| 4,511,677 | A | 4/1985 | Horton et al. | |
| 4,522,953 | A * | 6/1985 | Barby et al. | 521/64 |
| 4,611,014 | A | 9/1986 | Jomes et al. | |
| 5,723,508 | A | 3/1998 | Healy et al. | |
| 6,395,300 | B1 | 5/2002 | Straub et al. | |
| 6,645,528 | B1 | 11/2003 | Straub et al. | |
| 6,932,983 | B1 | 8/2005 | Straub et al. | |
| 2002/0041896 | A1 | 4/2002 | Straub et al. | |
| 2002/0142050 | A1 | 10/2002 | Straub et al. | |
| 2004/0096515 | A1 * | 5/2004 | Bausch et al. | 424/490 |
| 2005/0048116 | A1 | 3/2005 | Straub et al. | |
| 2005/0058710 | A1 | 3/2005 | Straub et al. | |

FOREIGN PATENT DOCUMENTS

| | | | | |
|---|---|---|---|---|
| EP | 1029886 | A2 | | 8/2000 |
| WO | 98/29100 | | | 7/1998 |
| WO | 99/00187 | | | 1/1999 |
| WO | PCT/US98/12797 | | * | 7/1999 |
| WO | 00/72827 | | | 12/2000 |
| WO | 01/19345 | | | 3/2001 |
| WO | 2004/011537 | A1 | | 2/2004 |
| WO | 2005/014704 | A1 | | 2/2005 |

OTHER PUBLICATIONS

Merriam Webster's Definition of Disperse: http://www.merriam-webster.com/dictionary/DISPERSE.*

Charlesby. Journal of Polymer Science vol. 11, Issue 6, pp. 513-520 (2003). http://onlinelibrary.wiley.com/doi/10.1002/pol.1953.120110601/pdf.*

International Search Report Application No. PCT/EP2004/014755 mailed May 31, 2005.

K. Whang et al.: A novel method to fabricate bioabsorbable scaffolds Polymer, Elsevier Science Publishers B. V. GB, pp. 837-842, XP004025968.

Search Report under Section 17 Application No. GB0401947.7 dated Jul. 20, 2004.

Japanese Patent Office Action for Application No. 2006-549919 dated Nov. 24, 2010 (4 pages).

* cited by examiner

*Primary Examiner* — Shanon A Foley
*Assistant Examiner* — Sarah Alawadi
(74) *Attorney, Agent, or Firm* — Michael Best & Friedrich LLP

(57) ABSTRACT

Porous bodies which are soluble or dispersible in non-aqueous media comprising a three dimensional open-cell lattice containing (a) 10 to 70% by weight of a polymeric material which is soluble in water immiscible non-aqueous media and (b) 30 to 90% by weight of a surfactant, said porous bodies having an intrusion volume as measured by mercury porosimetry of at least 3 ml/g.

8 Claims, No Drawings

POROUS BODIES AND METHOD OF PRODUCTION THEREOF

The present invention relates to porous bodies which are soluble or dispersible in non-aqueous media and to methods of producing such porous bodies.

Copending international patent application PCT/GB03/03226 (assigned to the present applicants) describes the formation of porous beads comprising a three dimensional open-cell lattice of a water-soluble polymeric material with an average bead diameter in the range 0.2 to 5 mm.

It is an object of the present invention to provide highly porous bodies which dissolve or disperse rapidly when contacted with non aqueous media. It is a further object of the invention to provide a simple and effective method for producing such porous bodies.

In accordance with a first aspect of the invention, there is provided porous bodies which are soluble or dispersible in non-aqueous media comprising a three dimensional open-cell lattice containing (a) 10 to 95% by weight of a polymeric material which is soluble in water immiscible non-aqueous media and (b) 5 to 90% by weight of a surfactant, said porous bodies having an intrusion volume as measured by mercury porosimetry (as hereinafter described) of at least 3 ml/g Preferably the porous bodies of the present invention contain 10 to 80% by weight of the polymeric material and 20 to 90% by weight of the surfactant. More preferably the porous bodies of the present invention contain 20 to 70% by weight of the polymeric material and 30 to 80% by weight of the surfactant.

It is also important for the operation of the present invention that the porous bodies dissolve or disperse quickly so that the materials contained within the lattice are dispersed quickly when the porous bodies are exposed to a non-aqueous medium. The nature of the lattice should be such that the dispersion of the porous bodies occurs in less than three minutes preferably less than 2 minutes, more preferably less than 30 seconds.

Suitable polymeric materials include homopolymers and copolymers made from one or more of the following (co) monomers:—

Alkenes for example ethylene or propylene; dienes for example butadiene; urethanes; vinyl esters for example vinyl acetate; styrenics for example styrene or alpha-methyl styrene; alkyl (methacrylates for example methyl methacrylate or butyl acrylate; alkyl (meth)acrylamides for example butyl acrylamide or decyl methacrylamide; (meth)acrylonitrile; vinyl ethers for example methyl vinyl ether, imides; amides; anhydrides, esters; ethers, carbonates; isothlocyanates; silanes; siloxanes; sulphones; aliphatic and aromatic alcohols for example ethylene glycol or 1,4-benzene dimethanol; aromatic and aliphatic acids for example phthalic acid or adipic add; aromatic and aliphatic amines for example hexamethylene diamine.

When the polymeric material is a copolymer it may be a statistical copolymer (heretofore also known as a random copolymer), a block copolymer, a graft copolymer or a hyperbranched copolymer. Comonomers other than those listed above may also be included in addition to those listed if their presence does not destroy the water insoluble nature of the resulting polymeric material.

Examples of suitable homopolymers include polyvinyl acetate, polystyrene, polyethylene, polypropylene, polybutadiene, polyethyieneterephthalate, nylon, polydimethylsiloxane, polybutylisocyanate, poly (1-octene-co-sulphur dioxide)

The surfactant may be non-ionic, anionic, catonic, non-ionic, or zwitterionic and is preferably solid at ambient temperature. Examples of suitable non-ionic surfactants include ethoxylated triglycerides; fatly alcohol ethoxylates; alkylphenol ethoxylates; fatty acid ethoxylates; fatty amide ethoxylates; fatty amine ethoxylates; sorbitan alkanoates; ethylated sorbitan alkanoates; alkyl ethoxylates; pluronics; alkyl polyglucosides; stearol ethoxylates. Examples of suitable anionic surfactants include alkylether sulfates; alkylether carboxylates; alkylbenzene sulfonates; alkylether phosphates; dialkyl sulfosuccinates; alkyl sulfonates; soaps; alkyl sulfates; alkyl carboxylates; alkyl phosphates; paraffin sulfonates; secondary n-alkane sulfonates; alpha-olefin sulfonates; isethionate sulfonates. Examples of suitable catonic surfactants include fatty amine salts; fatty diamine salts; quatemary ammonium compounds; phosphonium surfactants; sulfonium surfactants; sulfonxonium surfactants. Examples of suitable zwitterionic surfactants include N-alkyl derivatives of amino acids (such as glycine, betaine, aminopropionic acid); imidazoline surfactants; amine oxides; amidobetaines. Mixtures of surfactants may be used.

The bulk density of the porous polymeric bodies is preferably in the range of from about 0.01 to about 0.3 g/cm$^3$, more preferably from about 0.05 to about 0.2 g/cm$^3$, and most preferably from about 0.08 to about 0.15 g/cm$^3$.

The porous bodies of the present invention may be formed by freezing an intimate mixture (for example an emulsion) of the polymeric material and the surfactant in a liquid medium and freeze drying the resulting frozen mixture.

The porous bodies of the present invention disperse when exposed to a non-aqueous medium. The non-aqueous media to which the porous bodies are exposed may be any non-aqueous liquid into which the porous bodies can be dissolved or dispersed. The term "non-aqueous" as used herein includes liquids which contain minor amounts of water but which would be considered by those skilled in the art to be substantially non-aqueous. The non-aqueous media to which the porous bodies are exposed may be water-miscible or water immiscible. The non-aqueous media may be a water immiscible organic solvent for example alkanes such as heptane, n-hexane, isooctane, dodecane, decane; cyclic hydrocarbons such as toluene, xylene, cyclohexane; halogenated alkanes such as dichloromethane, dichoroethane, trichbromethane (chloroform), fluorotrichloromethane and tetrachloroethane; esters such as ethyl acetate; ketones such as 2-butanone; ethers such as diethyl ether, and mixtures thereof. Examples of suitable water miscible organic solvents include alcohols such as methanol, ethanol, isopropanol; and acetone; acetonitrile or tetrahydrofuran. Non-organic liquids such as volatile silicones (e.g. cydomethicone) may also be used as the non-aqueous media to which the porous bodies are exposed.

By including a polymeric material which is soluble in non-aqueous media in the lattice of porous bodies, porous bodies are formed which disperse rapidly in non-aqueous media. The polymeric material and any other components carried in the porous bodies will therefore become dispersed/dissolved in the non-aqueous medium. The provision of the porous bodies of the present invention facilitates the dissolution or dispersion of the materials contained in the porous bodies in non-aqueous media and the dissolution/dispersion is more rapid than is observed when the same materials are used but are not in the form required by the present invention.

The present invention also includes, in a further aspect, solutions or dispersions comprising polymeric materials and surfactant formed by exposing the porous bodies of the present invention to a non-aqueous medium.

The present invention also includes, in a further aspect, solutions or dispersions comprising polymeric materials, surfactant and a water-soluble (hydrophilic) material formed by exposing the porous bodies of the present invention having the hydrophilic material contained therein to a non-aqueous medium.

The porous bodies of the present invention may include within the lattice, water soluble materials which will be dispersed when the polymeric bodies are dispersed in a non-aqueous medium. The water soluble materials may be incorporated into the lattice by dissolving them in the liquid medium from which they are made. It has been found that the dispersion into a non-aqueous medium of water-soluble materials contained within the porous bodies of the present invention is much improved when the porous bodies are exposed to the non-aqueous medium. Examples of suitable water soluble materials include:— Water soluble vitamins such as vitamin C; water soluble fluorescers such as 4,4'-bis (sulfostyryl)biphenyl disodium salt (sold under the trade name Tinopal CBS-X; activated aluminium chlorohydrate; transition metal complexes used as bleaching catalysts; water soluble polymers such as modified polyesters of isophthalic acid), gerol, xanthan gum, jaguar or polyacrylates; diethylenetriamine pentaacetic acid; primary and secondary alcohol sulphates such as commercially examples eg cocoPAS or mixtures thereof The porous bodies of the present invention may include within the lattice water-insoluble materials which will be dispersed when the polymeric bodies are dispersed in an non-aqueous medium. The water-insoluble materials may be incorporated into the lattice by dissolving them in the continuous oil phase of a water-in-oil emulsion from which the lattice is made. Examples of suitable water insoluble materials include antimicrobial agents; antidandruff agent; skin lightening agents; fluorescing agents; antifoams; hair conditioning agents; fabric conditioning agents; skin conditioning agents; dyes; UV protecting agents; bleach or bleach precursors; antioxidants; insectides; pesticides; herbicides; perfumes or precursors thereto; flavourings or precursors thereto; pharmaceutically active materials; hydrophobic polymeric materials and mixtures thereof.

It may be required to disperse the hydrophilic materials at the point where the product is being used. In this case the porous bodies of the present invention will be contained in the product until it is used by exposing it to a non-aqueous environment, at which time the lattice of the porous body will break down releasing the hydrophilic material.

The porous bodies of the present invention may be used to introduce hydrophilic materials into products, for example, liquid products during the manufacture of the products. In this case the lattice of the porous bodies of the present invention will break down when the porous bodies contact a non-aqueous environment during manufacture releasing the hydrophilic material in a form in which it can be more readily incorporated into the product being manufactured.

The porous bodies of the present invention may be used to transport materials to sites where they can be incorporated into products. By converting liquid products into porous bodies the need to transport large amounts of liquids can be avoided resulting in significant cost savings and safer transport of materials which are potentially hazardous when transported in a liquid form. Materials which would be potentially unstable if stored or transported in liquid form may be incorporated into the porous bodies of the present invention and stored or transported with less risk of degradation.

The incorporation of potentially unstable hydrophilic materials into the porous bodies of the present invention may protect them from degradation during storage prior to use.

The intrusion volume of the porous bodies as measured by mercury porosimetry (as hereinafter described) is preferably at least about 4 ml/g, even more preferably at least about 5 ml/g, and most preferably at least about 6 ml/g. For example, the intrusion volume may be from about 3 ml/g to about 30 ml/g, preferably from about 4 ml/g to about 25 ml/g, more preferably from about 7 ml/g to about 20 ml/g. Intrusion volume provides a good measure of the pore volume in materials of this general type. The polymeric porous bodies may be in the form of powders, beads or moulded bodies. Powders may be prepared by the disintegration of porous bodies in the form of beads or moulded bodies.

In accordance with another aspect of the present invention, there is provided a method for preparing porous bodies which are soluble or dispersible in non-aqueous media comprising a three dimensional open-cell lattice containing (a) 10 to 95% by weight of a polymeric material which is soluble in water-immiscible non-aqueous media and (b) 5 to 90% by weight of a surfactant, said porous bodies having an intrusion volume as measured by mercury porosimetry (as hereinafter described) of at least 3 ml/g said process comprising the steps of a) providing an intimate mixture of the polymeric material and the surfactant in a liquid medium b) providing a fluid freezing medium at a temperature effective for rapidly freezing the liquid medium;

c) cooling the liquid medium with the fluid freezing medium at a temperature below the freezing point of the liquid medium for a period effective to rapidly freeze the liquid medium; and (d) freeze-drying the frozen liquid medium to form the porous bodies by removal of the liquid medium by sublimation.

The intimate mixture of the polymeric material and the surfactant in the liquid medium may be a water-in-oil emulsion comprising a continuous oil phase containing the polymeric material, a discontinuous aqueous phase and the surfactant;

When the porous body is to be in the form of a powder the cooling of the liquid medium may be accomplished by spraying an atomised liquid medium into the fluid freezing medium. When the porous body is to be in the form of beads the cooling of the liquid medium may be accomplished by dropping drops of the liquid medium into the fluid freezing medium. Porous bodies in the form of moulded bodies may be made by pouring the liquid medium into a mould and cooling the liquid medium by the fluid freezing medium. In a preferred process of the invention to make moulded bodies, the liquid medium is poured into a pre-cooled mould surrounded by fluid freezing medium.

The frozen liquid medium may be freeze-dried by exposing the frozen liquid medium to high vacuum. The conditions to be used, will be well known to those skilled in the art and the vacuum to be applied and the time taken should be such that all the frozen liquid medium present has been removed by sublimation. In the case of moulded porous polymeric bodies the freeze drying may take place with the frozen liquid medium still in the mould. Alternatively, the frozen liquid medium may be removed from the mould and freeze-dried in a commercial freeze-drier. The freeze-drying step may be performed for up to around 72 hours in order to obtain the porous bodies of the present invention.

The above process preferably uses a water-in-oil emulsion which comprises a continuous oil phase with the polymeric material dissolved therein, a discontinuous aqueous phase and the surfactant which is to be incorporated into the porous bodies of the present invention and which acts as an emulsifier for the emulsion. Preferably, the polymeric material is present in the continuous phase in a concentration of about 1% to 50% by weight. Even more preferably, the polymeric material is present in the continuous phase in a concentration of about 3% to 10% by weight.

Surfactants suitable for use as emulsifiers in water-in-oil emulsions preferably have an HLB value in the range 3 to 6. It is preferred that the surfactant is present in the liquid medium in a concentration of about 1% to about 60% by weight. More preferably, the surfactant is present in the liquid medium in a concentration of about 2% to about 40% by weight and a yet more preferred concentration is about 5% to about 25% by weight.

The continuous oil phase of the oil-in-water emulsion preferably comprises a material which is immiscible with the aqueous phase, which freezes at a temperature above the temperature which is effective for rapidly freezing the liquid medium and which is removable by sublimation during the freeze drying stage. The continuous oil phase of the emulsion may be selected from one or more from the following group of organic solvents:— alkanes such as heptane, n-hexane, isooctane, dodecane, decane; cyclic hydrocarbons such as toluene, xylene, cydohexane; halogenated alkanes such as dichloromethane, dichoroethane, trichloromethane (chloroform), fluorotrichloromethane and tetrachloroethane;

esters such as ethyl acetate;

ketones such as 2-butanone;

ethers such as diethyl ether;

volatile cyclic silicones such as cyclomethicone

Preferably, the aqueous phase comprises from about 10% to about 95% v/v of the emulsion, more preferably from about 20% to about 60% v/v.

In the process of the invention the fluid freezing medium is preferably inert to the polymeric material. Preferably, the fluid freezing medium is at a temperature below the freezing point of all of the components and is preferably at a much lower temperature to facilitate rapid freezing. The fluid freezing medium is preferably a liquified substance which is a gas or vapour at standard temperature and pressure. The liquified fluid freezing medium may be at its boiling point during the freezing of the liquid medium or it may be cooled to below its boiling point by external cooling means. The fluid freezing medium may be selected from one or more of the following group; liquid air, liquid nitrogen (b.p. −196° C.), liquid ammonia (b.p. −33° C.), liquified noble gas such as argon, liquefied halogenated hydrocarbon such as trichloroethylene, chlorofluorocarbon, freon, hexane, dimethylbutene, isoheptane or cumene. Mixtures of organic liquids and solid carbon dioxide may also be used as the fluid freezing medium. Examples of suitable mixtures include chloroform or acetone and solid carbon dioxide (−77° C. and diethyl ether and solid carbon dioxide (−100° C.). The fluid medium is removed during freeze drying preferably under vacuum and may be captured for reuse. Due to the very low boiling temperature, inertness, ease of expulsion and economy, liquid nitrogen is the preferred fluid freezing medium.

The emulsions are typically prepared under conditions which are well known to those skilled in the art, for example, by using a magnetic stirring bar, a homogenizer, or a rotator mechanical stirrer.

The porous bodies produced usually comprise of two types of pores which are produced during the freeze drying step. One is from the sublimation of the oil phase material. This pore structure can be varied by varying the polymer, the polymer molecular weight, the polymer concentration, the nature of the discontinuous phase and/or the freezing temperature. The other kind of pore structure results from the sublimation of the ice formed by the freezing of the water in the aqueous phase.

The method for producing porous bodies according to the present invention, will now be more particularly described, byway of example only, with reference to the accompanying Examples.

In the Examples that follow the intrusion volume and bulk density are measured by mercury porosimetry as described below and the dissolution time is measured as described below.

Mercury Porosimetry

Pore intrusion volumes and bulk densities were recorded by mercury intrusion porosimetry using a Micromeritics Autopore IV 9500 porosimeter over a pressure range of 0.10 psia to 60000.00 psia. Intrusion volumes were calculated by subtracting the intrusion arising from mercury interpenetration between beads (pore size >150 μm) from the total intrusion.

Dissolution Time

A weighed sample of the polymeric bodies was stirred gently with a non-aqueous solvent until the stirred mixture was clear to the eye. The time at which the mixture became clear to the eye was recorded as the dissolution time

EXAMPLE 1

An experiment was conducted in order to produce highly porous bodies which are soluble or dispersible in non-aqueous media in which the polymeric material is polyvinyl acetate. These bodies contained about 28.5% w/w polymer and about 71.5% w/w surfactant The bodies were prepared By freezing a water-in-oil emulsion in liquid nitrogen. The emulsion comprised a continuous toluene phase containing polyvinyl acetate and a discontinuous phase comprising water. Sodium dioctylsulfosuccinate (AOT) was used as the surfactant.

A 5% solution of polyvinyl acetate in toluene was prepared by adding polyvinyl acetate (PVAc $M_W$=83000) to toluene. A sample of the solution (2 ml) was stirred with a type RW11 Basic IKA paddle stirrer, and AOT (0.25 g) was added followed by water (6 ml) to form an emulsion having 75% v/v of discontinuous phase.

EXAMPLE 1A

The above emulsion was sprayed into liquid nitrogen from an airbrush. The frozen emulsion was placed in a freeze-drier overnight to give porous bodies in the form of a powder.

EXAMPLE 1B

The above emulsion was placed in a beaker which was placed in liquid nitrogen to freeze the emulsion. The frozen emulsion in the beaker was placed in a freeze drier overnight to give a porous moulded body shaped as the inside of the beaker.

EXAMPLE 2

An experiment was conducted in order to produce highly porous bodies which are soluble or dispersible in non-aqueous media in which the polymeric material is polyvinyl acetate. These bodies contained about 50% w/w polymer and about 50% w/w surfactant. The bodies were prepared by freezing a water-in-oil emulsion in liquid nitrogen. The emulsion comprised a continuous toluene phase containing polyvinyl acetate and a discontinuous phase comprising water. Sodium dioctylsulfosuccinate (AOT) was used as the surfactant.

A 5% solution of polyvinyl acetate in toluene was prepared by adding polyvinyl acetate (PVAc $M_w$=83000) to toluene. A sample of the solution (4 ml) was stirred with a type RW11 Basic IKA paddle stirrer, and AOT (0.2 g) was added followed by toluene (6 ml) to form an emulsion having 50% v/v of discontinuous phase.

A beaker was placed in a thermostatic vessel and liquid nitrogen was placed in both the beaker and the vessel. The emulsion prepared above was added dropwise from a needle to the liquid nitrogen in the beaker using a A-99 FZ Razel syringe pump. The beaker was placed in a freeze drier overnight to give spherical beads

EXAMPLE 3

An experiment was conducted in order to produce highly porous bodies in which the polymeric material is polystyrene (PS). The powder contained about 77% w/w polymer and about 23% w/w surfactant. These bodies were prepared by freezing a water-in-oil emulsion in liquid nitrogen. The emulsion comprised a continuous cyclohexane phase containing PS and a discontinuous aqueous phase. Dioctylsulfosuccinate (AOT) was used as the surfactant.

A 10% solution of PS was prepared by adding PS (ex Polysciences $M_w$=30000) to cyclohexane. A sample of the solution (2 ml) was stirred with a type RW11 Basic IKA paddle stirrer, and AOT (0.03 g/ml of PS solution) was added followed by water (6 ml) to form an emulsion having 75% v/v of discontinuous phase.

EXAMPLE 3A

The above emulsion was sprayed into liquid nitrogen from an airbrush. The frozen emulsion was placed in a freeze-drier overnight to give porous bodies in the form of a powder.

EXAMPLE 3B

The above emulsion was placed in a beaker which was placed in liquid nitrogen to freeze the emulsion. The frozen emulsion in the beaker was placed in a freeze drier overnight to give a porous moulded body shaped as the inside of the beaker.

EXAMPLE 4

An experiment was conducted in order to produce highly porous bodies in which the polymeric material is polystyrene (PS). The powder contained about 77% w/w polymer and about 23% w/w surfactant. These bodies were prepared by freezing a water-in-oil emulsion in liquid nitrogen. The emulsion comprised a continuous cyclohexane phase containing PS and a discontinuous aqueous phase. Dioctylsulfosuccinate (AOT) was used as the surfactant.

A 10% solution of PS in cyclohexane was prepared by adding PS (ex Polysciences $M_w$=30000) to cyclohexane. A sample of the solution (2 ml) was stirred with a type RW11 Basic IKA paddle stirrer, and AOT (0.06 g) was added followed by water (6 ml) to form an emulsion having 75% v/v of discontinuous phase. The above emulsion was placed in a beaker which was placed in liquid nitrogen to freeze the emulsion. The frozen emulsion in the beaker was placed in a freeze drier overnight to give a porous moulded body shaped as the inside of the beaker.

The intrusion volume and the bulk density were measured using mercury porosimetry as described above. The dissolution data was determined by taking a sample of the moulded body (0.1 g) in cyclohexane (2 ml) at 20'C. The results obtained are given in Table 1.

In a similar manner to that described above moulded bodies were prepared. The emulsions from which these bodies were prepared contained PS (2 ml-10 wt % solution in cyclohexane) and AOT (as set out in Table 1 below) and the appropriate volume of water

TABLE 1

| Ex. | Amount of Surfactant (g) | % discontinuous phase | % polymer | % surfactant | Intrusion volume (ml/g) | Dissolution time at 20° C. (min) | Bulk density (g/cm$^3$) |
|---|---|---|---|---|---|---|---|
| 4 | 0.06 | 75 | 77 | 23 | 5.73 | 0.58 | 0.14 |
| 4a | 0.0092 | 75 | 96 | 4 | | 1.42 | |
| 4b | 0.028 | 75 | 88 | 12 | | 1.63 | |
| 4c | 0.082 | 75 | 71 | 29 | | 1.67 | |
| 4d | 0.238 | 75 | 46 | 54 | | 2.58 | |
| 4e | 0.2 | 20 | 50 | 50 | | 0.42 | |
| 4f | 0.1 | 50 | 67 | 33 | | 0.75 | |

By way of comparison it has been observed that the polystyrene as supplied by the manufacturer had a dissolution time of around 58 minutes.

EXAMPLE 5

An experiment was conducted in order to produce highly porous bodies in which the polymeric material is polystyrene (PS). These bodies contained about 77% w/w polymer and about 23% w/w surfactant. These bodies were prepared by freezing a water-in-oil emulsion in liquid nitrogen. The emulsion comprised a continuous cyclohexane phase containing PS and a discontinuous aqueous phase. Sorbitan oleate (SPAN 80) was used as the surfactant.

A 10% solution of PS in cydohexane was prepared by adding PS (ex Polysciences $M_w$=30000) to cydohexane. A sample of the solution (3 ml) was stirred with a type RW11 Basic IKA paddle stirrer, and sorbitan oleate (0.1 ml ex Aldrich) was added followed by water (9 ml) to form an emulsion having 75% v/v of discontinuous phase.

The above emulsion was placed in a beaker which was placed in liquid nitrogen to freeze the emulsion. The frozen emulsion in the beaker was placed in a freeze drier overnight to give a porous moulded body shaped as the inside of the beaker.

In a similar manner to that described above moulded bodies were prepared from emulsions having 0%, 30% and 67 v/v of discontinuous phase. The emulsions from which these bodies were prepared using PS (3 ml-10 wt % solution in cydohexane) and sorbitan oleate (0.1 ml/3 ml PS solution) and the appropriate volume of water In the Table below the moulded body identified as containing 0% continuous phase was prepared from the PS solution and the sorbitan oleate with no water. The intrusion volume and the bulk density were measured using mercury porosimetry as described above. The dissolution data was determined by taking a sample of the moulded body (0.1 g) in cydohexane (2 ml) at 20° C. The results obtained are given in Table 2.

TABLE 2

| % Discontinuous phase | Intrusion Volume (ml/g) | Bulk density (g/ml) | Dissolution time at 20° C. (seconds) |
|---|---|---|---|
| 0 | 4.22 | 0.19 | 62 |
| 30 | 3.70 | 0.15 | 38 |
| 67 | | 0.27 | 42 |
| 75 | 2.76 | 0.27 | 14 |

By way of comparison it has been observed that the polystyrene as supplied by the manufacturer had a dissolution time of around 58 minutes.

EXAMPLE 6

An experiment was conducted in order to produce highly porous bodies in which the polymeric material is polystyrene (PS). These bodies contained about 71% w/w polymer and about 29% w/w surfactant These bodies were prepared by freezing a water-in-oil emulsion in liquid nitrogen. The emulsion comprised a continuous cyclohexane phase containing PS and a discontinuous aqueous phase. Steareth-2 (Brij-72) was used as the surfactant.

A 10% solution of PS in cydohexane was prepared by adding PS (ex Polysciences $M_w$=30000) to cydohexane. A sample of the solution (3 ml) was stirred with a type RW11 Basic IKA paddle stirrer, and steareth-2 (0.12 g) was added followed by water (9 ml) to form an emulsion having 75% v/v of discontinuous phase.

The above emulsion was placed in a beaker which was placed in liquid nitrogen to freeze the emulsion. The frozen emulsion in the beaker was placed in a freeze drier overnight to give a porous moulded body shaped as the inside of the beaker.

The intrusion volume and the bulk density were measured using mercury porosimetry as described above and were found to be 4.22 ml/g and 0.166 g/$cm^3$ respectively.

EXAMPLE 7

An experiment was conducted in order to produce highly porous bodies containing a hydrophilic dye, which bodies are soluble or dispersible in non-aqueous media in which the polymeric material is polyvinyl acetate. These bodies contained about 28% w/w polymer, about 69% w/w surfactant and about 3% dye. The bodies were prepared by freezing a water-in-oil emulsion in liquid nitrogen. The emulsion comprised a continuous toluene phase containing polyvinyl acetate and a discontinuous phase comprising water and the dye. Sodium dioctylsulfosuccinate (AOT) was used as the surfactant.

A 5% solution of polyvinyl acetate in toluene was prepared by adding polyvinyl acetate (PVAc $M_w$=83000) to toluene. A sample of the solution (2 ml) was stirred with a type RW11 Basic IKA paddle stirrer, and direct yellow 50 (0.01 g) and AOT (0.25 g) were added followed by water (6 ml) to form an emulsion having 75% v/v of discontinuous phase.

EXAMPLE 7A

The above emulsion was sprayed into liquid nitrogen from an airbrush. The frozen emulsion was placed in a freeze-drier overnight to give porous bodies in the form of a powder.

EXAMPLE 7B

The above emulsion was placed in a beaker which was placed in liquid nitrogen to freeze the emulsion. The frozen emulsion in the beaker was placed in a freeze drier overnight to give a porous moulded body shaped as the inside of the beaker.

EXAMPLE 7C

A beaker was placed in a thermostatic vessel and liquid nitrogen was placed in both the beaker and the vessel. The emulsion prepared above was added dropwise from a needle to the liquid nitrogen in the beaker using a A-99 FZ Razel syringe pump. The beaker was placed in a freeze drier overnight to give spherical beads

EXAMPLE 8

An experiment was conducted in order to produce highly porous bodies containing a hydrophobic dye, which bodies are soluble or dispersible in non-aqueous media in which the polymeric material is polyvinyl acetate. These bodies contained about 28% w/w polymer, about 69% w/w surfactant and about 3% dye. The bodies were prepared by freezing a water-in-oil emulsion in liquid nitrogen. The emulsion comprised a continuous toluene phase containing polyvinyl acetate and the dye and a discontinuous phase comprising water. Sodium dioctylsulfosuccinate (AOT) was used as the surfactant.

A 5% solution of polyvinyl acetate in toluene was prepared by adding polyvinyl acetate (PVAc $M_w$=83000) to toluene. A sample of the solution (2 ml) was stirred with a type RW11 Basic IKA paddle stirrer and solvent green 3 dye (0.01 g) and AOT (0.25 g were added followed by water (6 ml) to form an emulsion having 75% v/v of discontinuous phase.

EXAMPLE 8A

The above emulsion was sprayed into liquid nitrogen from an airbrush. The frozen emulsion was placed in a freeze-drier overnight to give porous bodies in the form of a powder.

EXAMPLE 8B

The above emulsion was placed in a beaker which was placed in liquid nitrogen to freeze the emulsion. The frozen emulsion in the beaker was placed in a freeze drier overnight to give a porous moulded body shaped as the inside of the beaker.

EXAMPLE 9

An experiment was conducted in order to produce highly porous bodies containing a hydrophobic dye, which bodies are soluble or dispersible in non-aqueous media in which the polymeric material is polyvinyl acetate. These bodies contained about 33% w/w polymer, about 54% w/w surfactant and 13% dye. The bodies were prepared by freezing a water-in-oil emulsion in liquid nitrogen. The emulsion comprised a continuous toluene phase containing polyvinyl acetate and the dye and a discontinuous phase comprising water. Sodium dioctylsulfosuccinate (AOT) was used as the surfactant.

A 2.5% solution of polyvinyl acetate in toluene was prepared by adding polyvinyl acetate (PVAc $M_w$=83000) to toluene. A sample of the solution (12 ml) was stirred with a type RW11 Basic IKA paddle stirrer and solvent green 3 dye (0.12 g) and AOT (0.5 g were added followed by water (12 ml) to form an emulsion having 75% v/v of discontinuous phase.

A beaker was placed in a thermostatic vessel and liquid nitrogen was placed in both the beaker and the vessel. The emulsion prepared above was added dropwise from a needle [Gauge 19] to the liquid nitrogen in the beaker using a A-99 FZ Razel syringe pump. The beaker was placed in a freeze drier overnight to give spherical beads [diameter 2-3 mm]

EXAMPLE 10

An experiment was conducted in order to produce highly porous bodies containing a hydrophilic dye, which bodies are soluble or dispersible in non-aqueous media in which the polymeric material is polystyrene. These bodies contained about 60% w/w polymer, about 16% w/w surfactant and about 24% w/w dye. The bodies were prepared by freezing a water-in-oil emulsion in liquid nitrogen. The emulsion comprised a continuous cyclohexane phase containing polystyrene and a discontinuous phase comprising water and the dye. Sodium dioctylsulfosuccinate (AOT) was used as the surfactant.

A 10% solution of polystyrene in cyclohexane was prepared by adding polystyrene (PS ex Polysciences Inc $M_w$=30000) to cyclohexane. A sample of the solution (2 ml) was stirred with a type RW11 Basic IKA paddle stirrer and AOT (0.054 g) and an aqueous solution of methyl orange (0.16 g) were added to form an emulsion having 50% v/v of discontinuous phase.

The above emulsion was sprayed into liquid nitrogen from an airbrush. The frozen emulsion was placed in a freeze-drier overnight to give porous bodies in the form of a powder.

The dissolution time was determined using a sample of the powder (0.1 g) in cyclohexane (2 ml) at 20° C. and was 22 seconds.

EXAMPLE 11

An experiment was conducted in order to produce highly porous bodies containing a hydrophobic dye, which bodies are soluble or dispersible in non-aqueous media in which the polymeric material is polystyrene. These bodies contained about 60% w/w polymer, about 16% w/w surfactant and about 24% w/w dye. The bodies were prepared by freezing a water-in-oil emulsion in liquid nitrogen. The emulsion comprised a continuous cyclohexane phase containing polystyrene and a discontinuous phase comprising water and the dye. Sodium dioctylsulfosuccinate (AOT) was used as the surfactant.

A 10% solution of styrene in cydohexane was prepared by adding polystyrene (PS ex Polysciences Inc $M_w$=30000) and oil blue dye (0.08 wt %) to cyclohexane. A sample of the solution (2 ml) was stirred with a type RW11 Basic IKA paddle stirrer and AOT (0.054 g) and water (2 ml) were added to form an emulsion having 50% v/v of discontinuous phase.

The above emulsion was sprayed into liquid nitrogen from an airbrush. The frozen emulsion was placed in a freeze-drier overnight to give porous bodies in the form of a powder.

The dissolution time was determined using a sample of the powder (0.1 g) in cyclohexane (2 ml) at 20° C. and was 11 seconds.

The invention claimed is:

1. Freeze-dried, water-in-oil emulsion-templated porous bodies each comprising a three dimensional open cell lattice which is soluble in non-aqueous media, said lattice containing (a) 10 to 95% by weight of a polymeric material which is soluble in the non-aqueous media and (b) 5 to 90% by weight of a surfactant which is soluble in the non-aqueous media, said porous bodies having an intrusion volume as measured by mercury porosimetry of at least about 3 ml/g; and comprising two types of pores:

(1) from the sublimation of solid ice from the water phase of the emulsion, and (2) from the sublimation of the oil phase of the emulsion, wherein a water-soluble material is incorporated into the lattice of said porous bodies to be dispersed in the non-aqueous media when said lattice dissolves, said lattice visually fully dissolving in the non-aqueous media in less than 3 minutes when 0.1 g of said porous bodies are stirred with 2 ml of the non-aqueous media at 20° C.

2. Porous bodies as claimed in claim 1 wherein the bodies are in the form of powders, beads or moulded bodies.

3. Porous bodies as claimed in claim 1 wherein the polymeric material is a homopolymer or copolymer made from one or more of the following (co)monomers: Alkenes; dienes; urethanes; vinyl esters; styrenics; alkyl (meth)acrylates; alkyl (meth)acrylamides; (meth)acrylonitrile; vinyl ethers; imides; amides; anhydrides, esters; ethers, carbonates; isothiocyanates; silanes; siloxanes; sulphones; aliphatic and aromatic alcohols; aromatic and aliphatic acids; aromatic and aliphatic amines.

4. Porous bodies as claimed in claim 3 wherein the polymeric material is a polystyrene homopolymer or polyvinyl acetate.

5. Porous bodies as claimed in claim 1 wherein the water soluble material is selected from water soluble vitamins; water soluble fluorescers; activated aluminium chlorohydrate; transition metal complexes used as bleaching catalysts; water soluble polymers; diethylenetriaminepentaacetic acid (DTPA); primary and secondary alcohol sulphates containing greater than C8 chain length or mixtures thereof.

6. Porous bodies as claimed in claim 1 further comprising a water insoluble material selected from the group consisting of antimicrobial agents; antidandruff agent; skin lightening agents; fluorescing agents; antifoams; hair conditioning agents; fabric conditioning agents; skin conditioning agents; dyes; UV protecting agents; bleach or bleach precursors; antioxidants; insecticides; pesticides; herbicides; perfumes or precursors thereto; flavourings or precursors thereto; pharmaceutically active materials; hydrophobic polymeric materials; and mixtures thereof.

7. Porous bodies as claimed in claim 1 wherein the lattice visually fully dissolves in the non-aqueous media in less than 30 seconds when 0.1 g of said porous bodies are stirred with 2 ml of the non-aqueous media at 20° C.

8. Porous bodies as claimed in claim 1 wherein said porous bodies are made by a process comprising the steps of:

a) providing an intimate mixture of the polymeric material, the surfactant, and the water-soluble material in a liquid medium;

b) providing a fluid freezing medium at a temperature effective for rapidly freezing the liquid medium;

c) cooling the liquid medium with the fluid freezing medium at a temperature below the freezing point of the liquid medium for a period effective to rapidly freeze the liquid medium; and d) freeze drying the frozen liquid medium to form the porous bodies by removal of the liquid medium by sublimation.

* * * * *